United States Patent [19]
Platts

[11] Patent Number: 5,481,804
[45] Date of Patent: Jan. 9, 1996

[54] RETRACTABLE-BLADED KNIFE

[76] Inventor: David Platts, 1932-B 42nd St., Los Alamos, N.M. 87544

[21] Appl. No.: 322,682

[22] Filed: Oct. 12, 1994

[51] Int. Cl.⁶ .................................................. A61B 17/32
[52] U.S. Cl. ............................... 30/162; 30/335; 606/167
[58] Field of Search ........................... 30/151, 162, 335; 606/172, 167

[56] References Cited

U.S. PATENT DOCUMENTS

| | | | |
|---|---|---|---|
| 3,577,637 | 5/1971 | Braginetz | 30/162 |
| 4,139,939 | 2/1979 | Crooks | 30/162 |
| 4,242,795 | 1/1981 | Rollband et al. | 30/162 |
| 4,621,425 | 11/1986 | Stoutenberg | 30/162 |
| 5,207,696 | 5/1993 | Matwijcow | 606/167 |
| 5,330,493 | 7/1994 | Haining | 606/167 |

FOREIGN PATENT DOCUMENTS 2704019  8/1978  Germany .................................. 30/335

Primary Examiner—Hwei Siu Payer
Attorney, Agent, or Firm—Samuel M. Freund

[57] ABSTRACT

A lightweight, slender knife having a replaceable, retractable cutting blade, which may be locked either in the operating or deployed position, or in a retracted or safety position, by using a single digit on one hand, is described. Safety of hospital personnel and medical waste-disposal personnel is achieved in the surgical scalpel embodiment of the present knife without loss of function or convenience of the scalpel. An automatically retracting embodiment of the knife is also described.

4 Claims, 5 Drawing Sheets

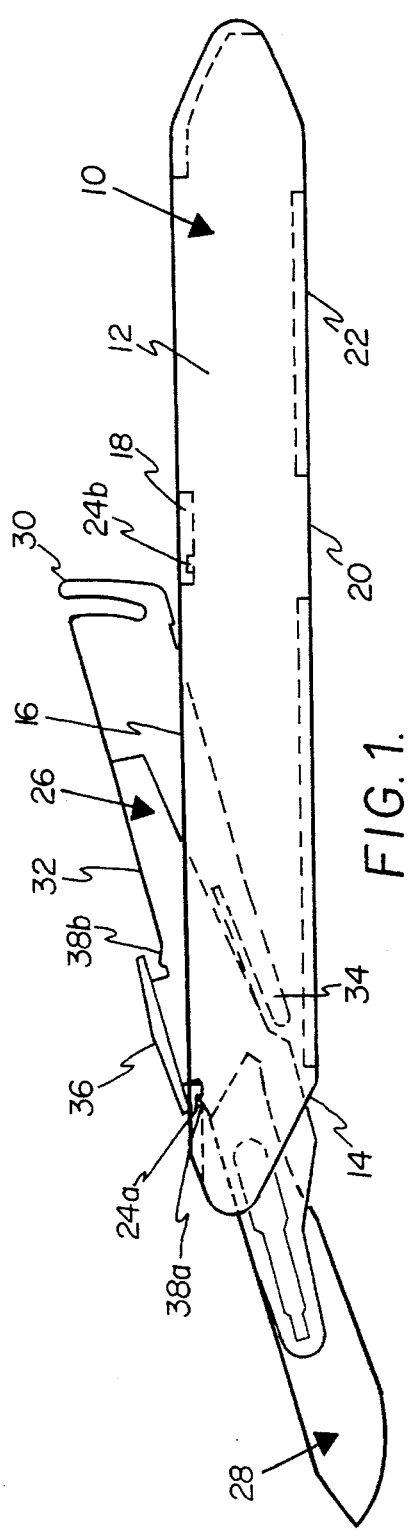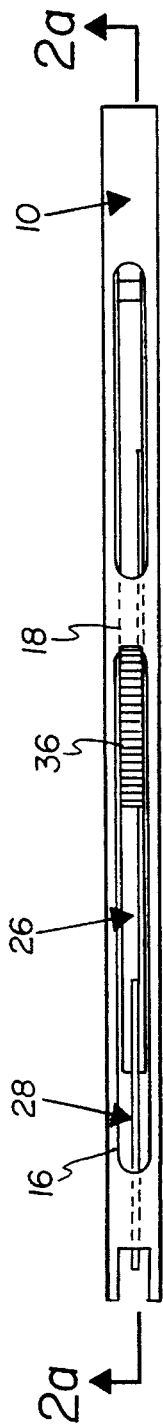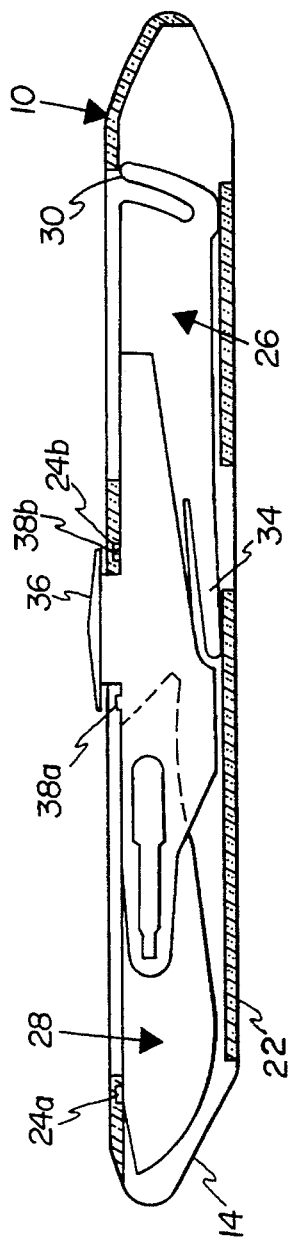

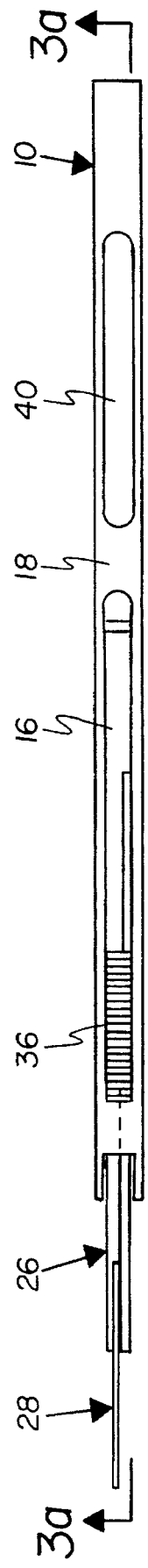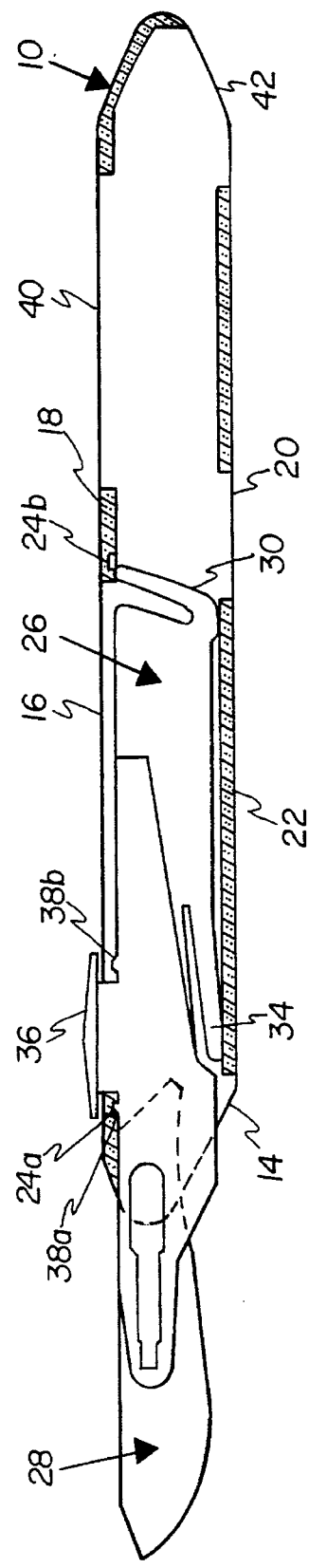
FIG. 3b.
FIG. 3a.

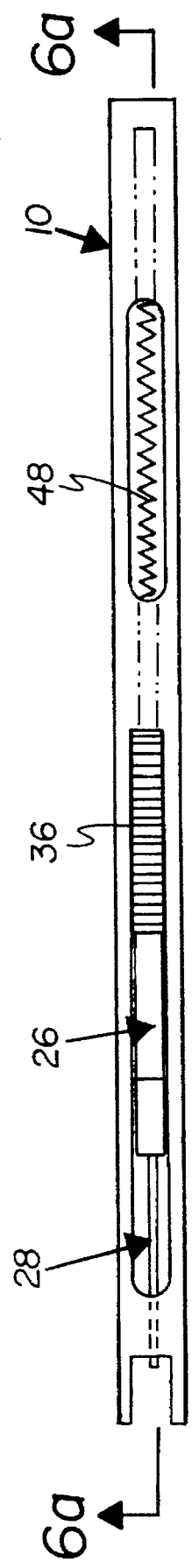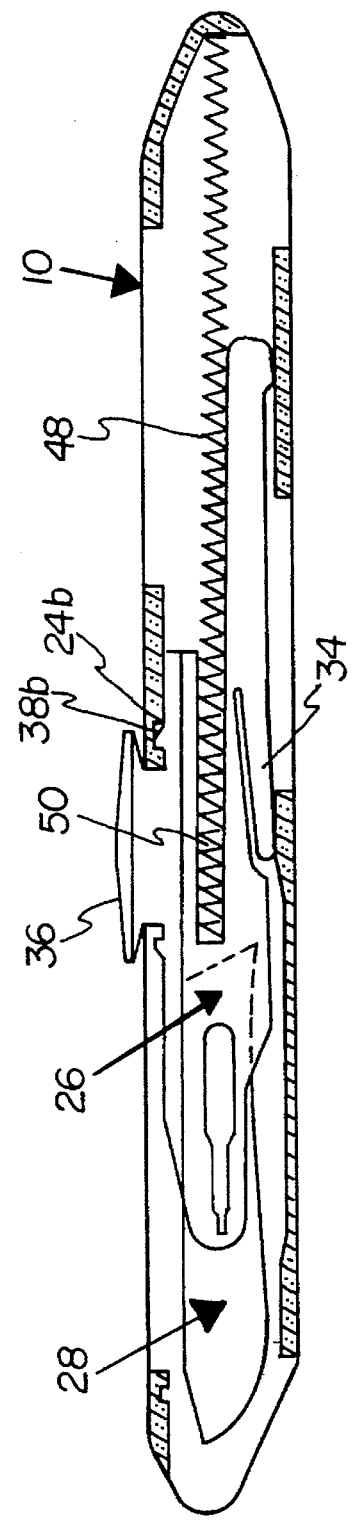

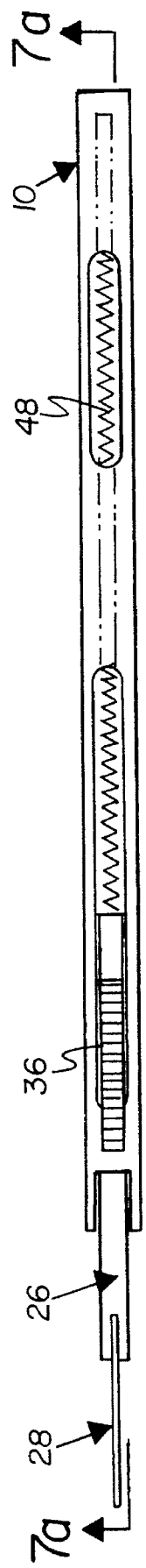
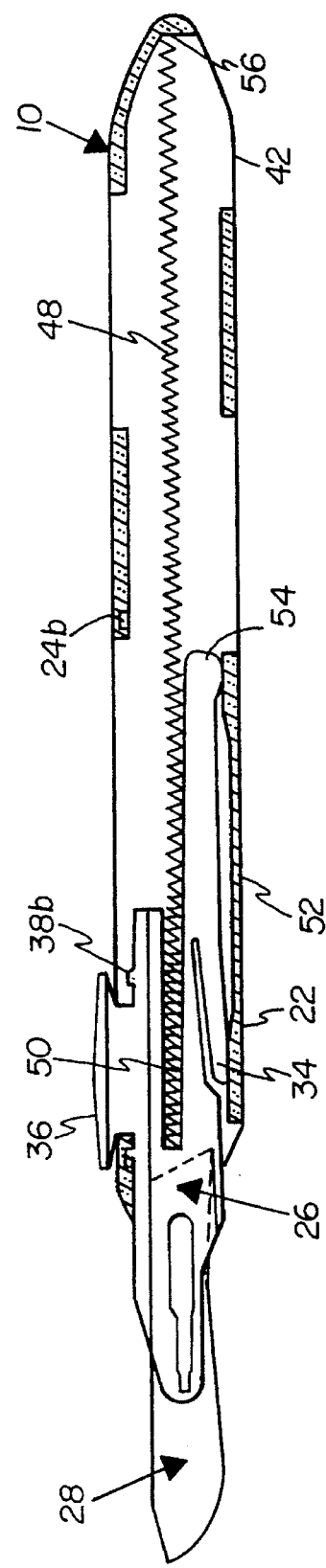

RETRACTABLE-BLADED KNIFE

BACKGROUND OF THE INVENTION

The present invention relates generally to cutting instruments, other knives and more particularly to surgical scalpels and having retractable blades.

It is well known that existing surgical cutting implements provide a significant potential for harm to surgeons and support personnel. That is, with attention directed toward the patient, rapid handling of surgical instruments with exposed sharp edges occasionally leads to cuts and puncture wounds, and more often to loss of integrity of surgical gloves. With increasing risk of life-threatening infectious diseases, it is imperative that such risks be minimized.

Utility knives having retractable blades are well known. The majority of such knives are operated utilizing actuating mechanisms located on the flat faces thereof. A relatively small number of knives having actuating mechanisms on their narrow edges are described. In U.S. Pat. No. 5,207,696 for "Surgical Scalpel ," which issued to Robert J. Matwijcow on May 4, 1993, the inventor describes a scalpel including a blade carrier and a blade shield equally movable in opposite longitudinal directions in response to longitudinal movement of an actuator along the upper edge of the scalpel housing. U. S. Pat. No. 3,577,637 for "Retractable Blade Knife," which issued to Fred A. Braginets on May 4, 1971 describes an industrial blade holder combination with the blade being mounted on a carrier and selectively movable to retracted and operative positions. Extending to the rear of the blade carrier is a flexible leaf spring portion carrying a manually engageable tab or fingerpiece connected to the spring portion by a rectangular, support. The leaf portion also carries a pair of upstanding latching lugs disposed to the side of the fingerpiece. Two opposed handle halves are cut away to form a longitudinally extending slot in the top edge thereof along which the rectangular portion of the fingerpiece may move. The handle halves also have cutaway portions extending longitudinally in the top edge to form opposed recesses into which the fingerpiece may be depressed to release the latching means. A similar actuating mechanism is described in U.S. Pat. No. 4,621,425 for "Retractable Knife Handle," which issued to Carl C. Stautenberg on Nov. 11, 1986.

The blade slides described in these patents are complex and wide in order to accommodate the latching mechanisms, and consequently wide handle portions must be fabricated from more than one part in order to receive these complex slides.

Accordingly, it is an object of the present invention to provide slender surgical scalpels and other knives having retractable blades which may be locked in either a deployed or a retracted position.

Another object of our invention is to provide slender surgical scalpels and other knives having retractable blades which may be locked in either. a deployed or a retracted position and which may be operated using one digit of one hand utilizing a digit-engaging tab located on the top edge thereof.

Yet another object of the invention is to provide slender surgical scalpels and other knives having retractable blades which may be locked in either a deployed or retracted position, but which cannot accidentally be deployed.

Still another object of our invention is to provide slender surgical scalpels and other knives having retractable blades for which standard, commercially-available blades are employed, and which have only three parts.

A further object of the invention is to provide slender surgical scalpels and other knives which are automatically retracted by depressing a finger-actuated tab on the top edge thereof.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the retractable-bladed knife hereof includes a generally flat, elongated handle having a forward end and a rearward end, and further having two generally flat, parallel sides separated by a narrow top edge having an inner surface and a narrow bottom edge having an inner surface such that an elongated cavity extending substantially over the long dimension of the handle and opening to the outside at the forward end thereof is formed, the top edge having an elongated notch therethrough toward the forward end of the handle, there being formed a first indentation in the inner surface of the top edge forward of the notch and a second indentation in the inner surface of the top edge behind the notch, and the bottom edge having a notch therethrough in order to enable the second indentation in the top edge to be formed therein; a cutting blade; and a flat, elongated slide adapted to slidably move longitudinally through the cavity in the handle and adapted to receive the cutting blade, the slide member having a generally straight top edge and an opposing bottom edge, and a digit-engaging tab protruding from the top edge adapted to extend through the notch in the top edge of the handle such that the digit-engaging tab may be engaged by and actuated by a digit of the operator of the knife, the slide member having first tab located toward the blade-receiving end thereof from the digit-engaging tab and adapted to engage the first indentation in the top portion of the handle, and a second tab located away from the blade-receiving end of the slide from the digit-engaging tab and adapted to engage the second indentation in the top portion of the handle, the slide further having a resilient, deformable tang projecting from the bottom portion thereof and opposing the digit-engaging tab such that the straight top edge of the slide is forced against the inner surface of the top portion of the handle by the action of the deformable portion of the slide against the inner surface of the bottom portion of the handle.

It is preferred that the blade be removable from the slide in order to permit fresh blades to be installed.

Preferably, a coil spring is located within the cavity of the handle along the long dimension thereof and attached to the end of the slide away from the blade-receiving end and to the handle in the vicinity of its closed end, thereby providing a force on the slide member directed toward the rearward end of the handle which automatically withdraws the slide from its deployed position when the digit-engaging tab is depressed and into the handle.

Benefits and advantages of the present invention include simple and inexpensive fabrication and assembly resulting from the simple, three-piece design.

BRIEF DESCRIPTION OF THE DRAWINGS

The accompanying drawings, which are incorporated in and forms a part of the specification, illustrate two embodiments of the present invention and, together with the description, serve to explain the principles of the invention.

FIG. 1 shows a schematic representation of a side view of the scalpel embodiment of the retractable-bladed knife of the present invention illustrating the installation of the blade/slide assembly into the handle cavity.

FIGS. 2a and 2b show schematic representations of a side view of the scalpel shown in FIG. I hereof in its closed, locked position, and the top view thereof, respectively.

FIGS. 3a and 3b schematic representations of a side view of the scalpel shown in FIG. 1 hereof and the top view thereof, respectively, and illustrate the blade-deployed mode thereof.

FIGS. 6a and 6b show schematic representations of side and top views, respectively, of an automatically-retracting surgical scalpel embodiment of the retractable-bladed knife of the present invention in its blade-retracted mode, and illustrate a coil spring utilized for withdrawing the slide into the handle cavity when the locking mechanism is depressed.

FIGS. 7a and 7b show schematic representations of side and top views, respectively, of the knife shown FIGS. 6a and 6b hereof in its blade-deployed condition.

DETAILED DESCRIPTION OF THE INVENTION

Figure 4:
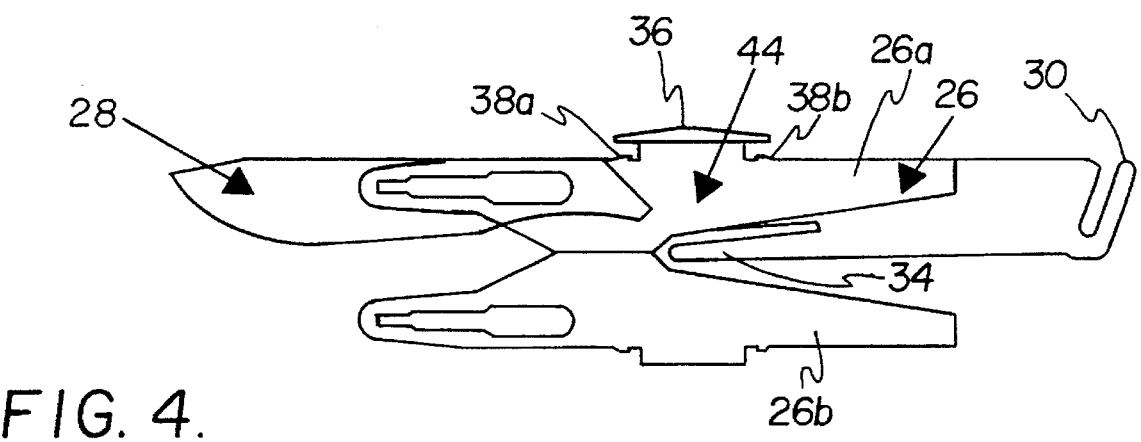
FIG. 4 is a schematic representation of a side view of one embodiment of the slide of the present retractable-bladed knife, and illustrates the blade/slide assembly in its pre-welded form.

Briefly, the present invention includes a lightweight, slender. cutting knife having a retractable blade which may be locked in either the operating or deployed position, or in a retracted or safety position, using a single digit on one hand. An automatically), retracting embodiment thereof is also described.

Reference will now be made in detail to the present preferred embodiments of the invention, an example of which is illustrated in the accompanying drawings. Identical or similar. structure is identified the same callouts.

FIG. 1 shows a side schematic representation of a surgical scalpel embodiment of the re tractable-bladed knife of the present invention illustrating the assembly of the three principal parts thereof. This embodiment will be used to illustrate the features of the retractable-bladed knife hereof, throughout. Handle 10 is generally flat and elongated in the embodiment thereof suitable for surgical procedures, among other uses. Cavity 12 is formed inside the handle and opens at the front end 14 thereof. Elongated s lot 16 permits the cavity, to open through the wall 18 of the top edge of the handle and slot 20 allows it to open through the wall 22 of the bottom edge thereof. Notches 24a and 24b are located in the inner surface of wall 18, notch 24b being through slot 20, while notch 24a is fashioned through front end 14. Slide 26 to which blade 28 is attached is shown with its forward end being inserted into the handle cavity through slot 16. Resilient, deformable tang 30 engages the inside of wall 18 once the long dimension of the slide is located parallel to the lone dimension of the handle. In this manner, the slide is stably located within the cavity when the blade is in its retracted position. Resilient, deformable tang 34, which projects below the bottom edge of slide 26, engages the inner surface of wall 22 and provides an upward force on the slide member to cause the upper edge 32 thereof to press firmly against the inner surface of wall 18, yet permit the slide to be readily moved within the handle cavity. A finger-engaging tab 36, and latching tabs 38a and 38b are also located on the top edge 32 of slide 26. Finger-engaging tab 36 protrudes through elongated slot 16 in the handle and may be engage by a digit of the operator of the knife to cause the slide to move within the cavity in either direction. When slide 26 is caused to move to its extreme forward position, wherein blade 28 is deployed, tab 38a and notch 24a automatically engage, as a result of the action of tang 34, and lock the slide in this position for use. When it is desired to withdraw the slide into the handle cavity, thereby completely shielding blade 28, finger-engaging tab 36 is depressed. This counters the action of tang 34 by forcing the upper edge of the slide away from the inner surface of wall 18, thereby releasing tab 38a from notch 24a and permitting the slide to be moved into the cavity by the operator. When the slide is moved to its extreme rearward position, tab 38b automatically engages notch 24b because of the upward action of tang 34, thereby preventing slide 26 from accidentally moving forward. When deployment of blade 28 is desired, tab 36 is pressed downward by the operator, thereby releasing tab 38b from notch 24b against the action of tang 34, and slide 26 may be moved forward in the handle cavity.

Slide 26 may be removed from the handle cavity for replacement, when blade 28 becomes dull or otherwise unsuitable for use, by depressing tang 30 through slot 20 in hand 10.

FIGS. 2a and 2b show schematic representations of side and top views, respectively, of the subject scalpel its closed, locked position.

FIGS. 3a and 3b show schematic representations of a side view and top view, respectively, of the scalpel and illustrate its blade-deployed, or open, locked position. Slots 40 and 42, along with slots 16 and 20, and front-end opening 14 permit handle 10 to be molded in one process step with cavity 12 and indentations or notches 24a and 24b in place.

FIG. 4 is a schematic representation of a side view of one embodiment of the slide and illustrates the blade/slide assembly in its pre-welded form. Shown is slide 26 having been molded in two attached sections, 26a and 26b, with blade 28 subsequently being installed on one of the sections. The two sections are then folded together and welded, thereby rigidly capturing blade 28 as slide/blade assembly 44. If it is now desired to change blades, slide/blade assembly 44 is removed from the handle, and discarded, being replaced by a new slide/blade assembly.

Figure 5:
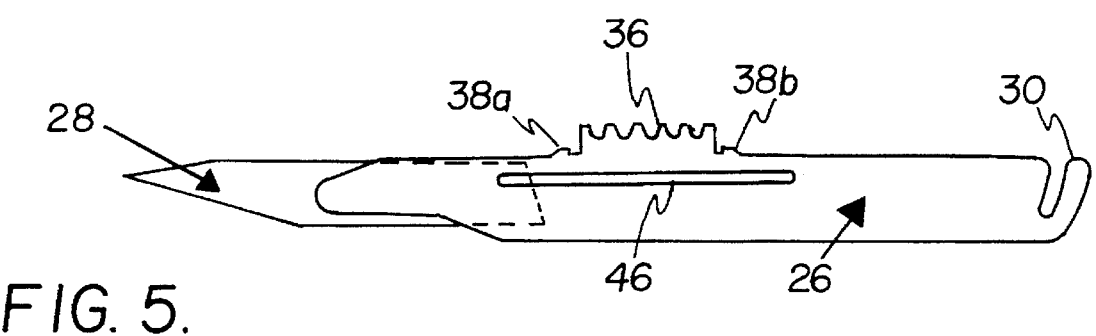
FIG. 5 is a schematic representation of a side view of a second embodiment of the slide, and illustrates an alternative manner in which slide latching may be achieved.

FIG. 5 is a schematic representation of the side view of a second embodiment of slide 26. Slot 46 permits the automatic, reversible engaging of latching tabs 38a and 38b with notches 24a and 24b, respectively, when slide 26 is moved to its forward or rearward positions in handle 10, respectively. When finger-engaging tab 36 is depressed, the latching action is released, since slide 26 is deformable as a result of the placement of slot 46. Slot 46, thereof acts in a similar manner to tang 34 shown in FIGS. 1–hereof by permitting the upper edge of the slide to be forced away from the inner Surface of wall 18 when finger-engaging tab 36 is depressed, thereby releasing tabs 38a and 38b from engaging notches 24a and 24b, respectively, and permitting the slide to be moved. When finger-engaging tab 36 is released, the upper edge of slide 26 will automatically engage the inner surface of wall 18 so that the tabs will engage their respective notches when in the appropriate positions.

FIGS. 6a and 6b are schematic representations of side and top views, respectively, of an automatically-retracting embodiment of the retractable-bladed surgical scalpel of the present invention in its blade-retracted condition, and illustrate coil spring 48, stretched between slide 26 and the rearward interior of handle 10, being utilized for withdrawing the slide into the handle cavity when finger-engaging tab 36 is depressed. Slide 26 is adapted by means of slot 50 to receive coil spring 48, such that a longer spring may be utilized in order to prevent the elastic limit thereof being exceeded.

FIGS. 7a and 7b are schematic representations of side and top views, respectively, of the automatically-retracting embodiment of the present invention shown in FIGS. 6a and 6b hereof in its blade-deployed condition, The lower wall 22 of handle 10 is relieved 52 such that when finger-engaging tab 36 is depressed, slide 26 will automatically move rearward with a speed which permits latching tab 38b to engage notch 24b handle 10, thereby preventing blade 28 from moving forward if the surgical scalpel is accidentally dropped. Raised portion 54 in the lower surface of slide 26 assists stabilizing slide 26 with respect to motion toward the top or bottom edges of handle 10 when the knife is in use. in both its forward and rearward latched positions. Spring 48 may be attached to the rear of handle 10 at point 56 through s lot 42, once slide 26 is installed into the cavity thereof.

The foregoing description of two preferred embodiments of the invention have been presented for purposes of illustration and description. It is not intended to be exhaustive or to limit the invention to the precise form disclosed, and obviously many modifications and variations are possible in light of the above teaching. For example, it would be apparent to one having skill in the surgical arts, after carefully studying the present disclosure, that various handle shapes and sizes and numerous cutting blade designs may be utilized in the present invention. Additionally, choice of materials would depend on the intended use; for example, biocompatible and sterilizable materials would be utilized for surgical instrument embodiments of the invention. The embodiments were chosen and described in order to best explain the principles of the invention and its practical application to thereby enable others skilled in the art to best utilize the invention in embodiments and with various modifications as are suited to the particular use contemplated. It is intended that the scope of the invention be defined by the claims appended hereto.

What is claimed is:

1. A knife, comprising in combination:
   a. a generally flat, elongated handle member having a forward end and a rearward end, and further having two generally flat, parallel sides separated by a narrow top portion having an inner surface and a narrow bottom portion having an inner surface such that an elongated cavity extending substantially over the long dimension of said handle member and opening to the outside at the forward end thereof is formed, the top portion having an elongated notch therethrough toward the forward end of said handle member, there being formed a first indentation in the inner surface of the top portion forward of the notch and a second indentation in the inner surface of the top portion behind the notch, and the bottom portion having a notch therethrough in order to enable the second indentation in the top portion to be formed therein;
   b. a cutting blade; and
   c. a flat, elongated slide member adapted to slidably move longitudinally through the cavity in said handle member and adapted to receive said cutting blade, said slide member having a generally straight top portion along the narrow dimension thereof and an opposing bottom portion, and a digit-engaging tab protruding from the top portion adapted to extend through the notch in the top portion of said handle member such that the digit-engaging tab may be engaged by and actuated by a digit of an operator of said knife, said slide member having a first tab located toward one end of said slide member adapted to receive said cutting blade from the digit-engaging tab and adapted to engage the first indentation in the top portion of said handle member, and a second tab located away from said one end of said slide member adapted to receive said cutting blade from the digit-engaging tab and adapted to engage the second indentation in the top portion of said handle member, said slide member further having a resilient, deformable tang projecting from the bottom portion thereof and opposing the digit-engaging tab such that the straight top portion of said slide member is forced against the inner surface of the top portion of said handle member by the action of the deformable tang of said slide member against the inner surface of the bottom portion of said handle member.

2. The knife as described in Claim 1, wherein said slide member is adapted to removably receive said cutting blade.

3. A knife, comprising in combination:
   a. a generally flat, elongated handle member having a forward end and a rearward end, and further having two generally flat, parallel sides separated by a narrow top portion having an inner surface and a narrow bottom portion having an inner surface such that an elongated cavity extending substantially over the long dimension of said handle member and opening to the outside at the forward end thereof is formed, the top portion having an elongated notch therethrough toward the forward end of said handle member, there being formed a first indentation in the inner surface of the top portion forward of the notch and a second indentation in the inner surface of the top portion behind the notch, and the bottom portion having a notch therethrough in order to enable the second indentation in the top portion to be formed therein;
   b. a cutting blade;
   c. a flat, elongated slide member adapted to slidably move longitudinally through the cavity in said handle member and adapted to receive said cutting blade, said slide member having a generally straight top portion along the narrow dimension thereof and an opposing bottom portion, and a digit-engaging tab protruding from the top portion adapted to extend through the notch in the top portion of said handle member such that the digit-engaging tab may be engaged by and actuated by a digit of an operator of said knife, said slide member having a first tab located toward one end of said slide member adapted to receive said cutting blade from the digit-engaging tab and adapted to engage the first indentation in the top portion of said handle member, and a second tab located away from said one end of said slide member adapted to receive said cutting blade from the digit-engaging tab and adapted to engage the second indentation in the top portion of said handle member, said slide member further having a resilient, deformable tang projecting from the bottom portion thereof and opposing the digit-engaging tab such that the straight top portion of said slide member is forced against the inner surface of the top portion of said handle member by the action of the deformable tang against the inner surface of the bottom portion of said handle member; and d. coil spring means located within the cavity of said handle member disposed generally along the long dimension thereof and adapted to engage said slide member in the vicinity of the end thereof away from the said one end adapted to receive said cutting blade and said handle member in the vicinity of the rearward end thereof, thereby providing a force on said slide member directed toward the rearward end of said handle member.

4. The knife as described in Claim 3, wherein said slide member is adapted to removably receive said cutting blade.

* * * * *